(12) United States Patent
Bettesh et al.

(10) Patent No.: US 8,348,830 B2
(45) Date of Patent: Jan. 8, 2013

(54) IN VIVO SENSING DEVICES AND METHODS OF IDENTIFICATION THEREOF

(75) Inventors: Ido Bettesh, Zichron Yacov (IL); Micha Nisani, Ramot Itzhak (IL); Boaz Aizenshtark, Shimshit (IL)

(73) Assignee: Given Imaging Ltd., Yoqneam (IL)

( * ) Notice: Subject to any disclaimer, the term of this patent is extended or adjusted under 35 U.S.C. 154(b) by 1305 days.

(21) Appl. No.: 12/101,295

(22) Filed: Apr. 11, 2008

(65) Prior Publication Data

US 2008/0255635 A1    Oct. 16, 2008

Related U.S. Application Data

(60) Provisional application No. 60/907,604, filed on Apr. 11, 2007.

(51) Int. Cl.
*A61B 1/00* (2006.01)
*A61B 1/04* (2006.01)

(52) U.S. Cl. .................................................. 600/117
(58) Field of Classification Search .............. 600/109, 600/117, 160, 302
See application file for complete search history.

(56) References Cited

U.S. PATENT DOCUMENTS

| | | |
|---|---|---|
| 4,278,077 A | 7/1981 | Mizumoto |
| 5,604,531 A | 2/1997 | Iddan et al. |
| 5,993,378 A | 11/1999 | Lemelson |
| 6,240,312 B1 | 5/2001 | Alfano et al. |
| 7,009,634 B2 | 3/2006 | Iddan et al. |
| 7,354,397 B2 | 4/2008 | Fujita et al. |
| 2002/0103417 A1 | 8/2002 | Gazdzinski |
| 2003/0213495 A1 | 11/2003 | Fujita et al. |
| 2005/0261551 A1 | 11/2005 | Couvillon et al. |
| 2006/0146739 A1 | 7/2006 | Matsumoto et al. |
| 2006/0149126 A1 | 7/2006 | Ertas et al. |
| 2009/0012360 A1* | 1/2009 | Kimoto et al. ................. 600/118 |

FOREIGN PATENT DOCUMENTS

| | | |
|---|---|---|
| DE | 344 0177 | 5/1986 |
| JP | 57-45833 | 3/1982 |
| JP | 02-31738 | 2/1990 |
| JP | 4-109927 | 4/1992 |
| JP | 1992-144533 | 5/1992 |

OTHER PUBLICATIONS

European search report of application No. 08 15 4317 issued on Jul. 23, 2008.

* cited by examiner

*Primary Examiner* — Philip R Smith
(74) *Attorney, Agent, or Firm* — Pearl Cohen Zedek Latzer, LLP

(57) ABSTRACT

An in-vivo sensing device for capturing sensed data of the gastrointestinal tract, or other body lumens or cavities of a patient, and for transmitting the sensed data to a data recorder external to the patient. The in-vivo sensing device has an identifier code associated with it. The sensed data may be transmitted to the data recorder together with the identifier code so that the received sensed data can be correlated with the in-vivo sensing device.

10 Claims, 5 Drawing Sheets

US 8,348,830 B2

IN VIVO SENSING DEVICES AND METHODS OF IDENTIFICATION THEREOF

CROSS REFERENCE TO RELATED APPLICATIONS

This application claims the benefit of Unites States Provisional Application Ser. No. 60/907,604, filed Apr. 11, 2007, which is hereby incorporated by reference in its entirety.

FIELD OF THE MENTION

The present invention relates in to in-vivo sensing devices that may communicate data to recording devices and methods of identifying the in-vivo sensing devices so that the recording devices are able associate received data with a given in-vivo sensing device.

BACKGROUND OF THE INVENTION

In-vivo sensing devices such as, for example, ingestible sensing capsules, for diagnosis of the gastrointestinal (GI) tract or other body lumens of a patient may wirelessly transmit sensed data, such as imaging data, to an external data recorder. The data recorder may be affixed to the patient by a strap or a belt so that the patient may freely perform normal actions during an observation period that may begin after swallowing of the in-vivo sensing device and end upon its excretion. The data recorder may have radio communication capability and it may have connected to it one or more antennas for receiving the sensed data transmitted by the in-vivo sensing device and the data recorder may have a memory for storing the received sensed data. After the observation period, the patient may deliver the data recorder to an operator, for example, a health professional who may download the stored sensed data for processing and for performing analysis of the GI tract for diagnosis purposes. The sensed data may include image data of images of the GI tract captured by an imager in the in-vivo sensing device as it passes through the GI tract.

The sensed data may be downloaded from the data recorder to a workstation, or the like, in order to analyze the images of the GI tract for diagnosis purposes. After the sensed data is downloaded to the workstation the image data has to undergo various forms of image processing in the workstation before the images can be diagnosed.

Clearly, a given in-vivo sensing device preferably communications data to a given data recorder. However, should another in-vivo sensing device be within communicating distance with the given data recorder, then it may have data communicated to it by the other in-vivo sensing device in addition to the data communicated to it by the given in-vivo sensing device, leading to possible confusion when analyzing the received data.

SUMMARY OF THE INVENTION

According to embodiments of the present invention an in-vivo sensing device is provided with an identifier code, such as, for example, but not limited to, a numeric string of characters or an alphanumeric string of characters. The in-vivo device may communicate data to a data recorder. The data may be communicated to the data recorder together with the identifier code.

BRIEF DESCRIPTION OF THE DRAWINGS

The present invention will be understood and appreciated more fully from the following detailed description taken in conjunction with the drawings in which.

Figure 1:
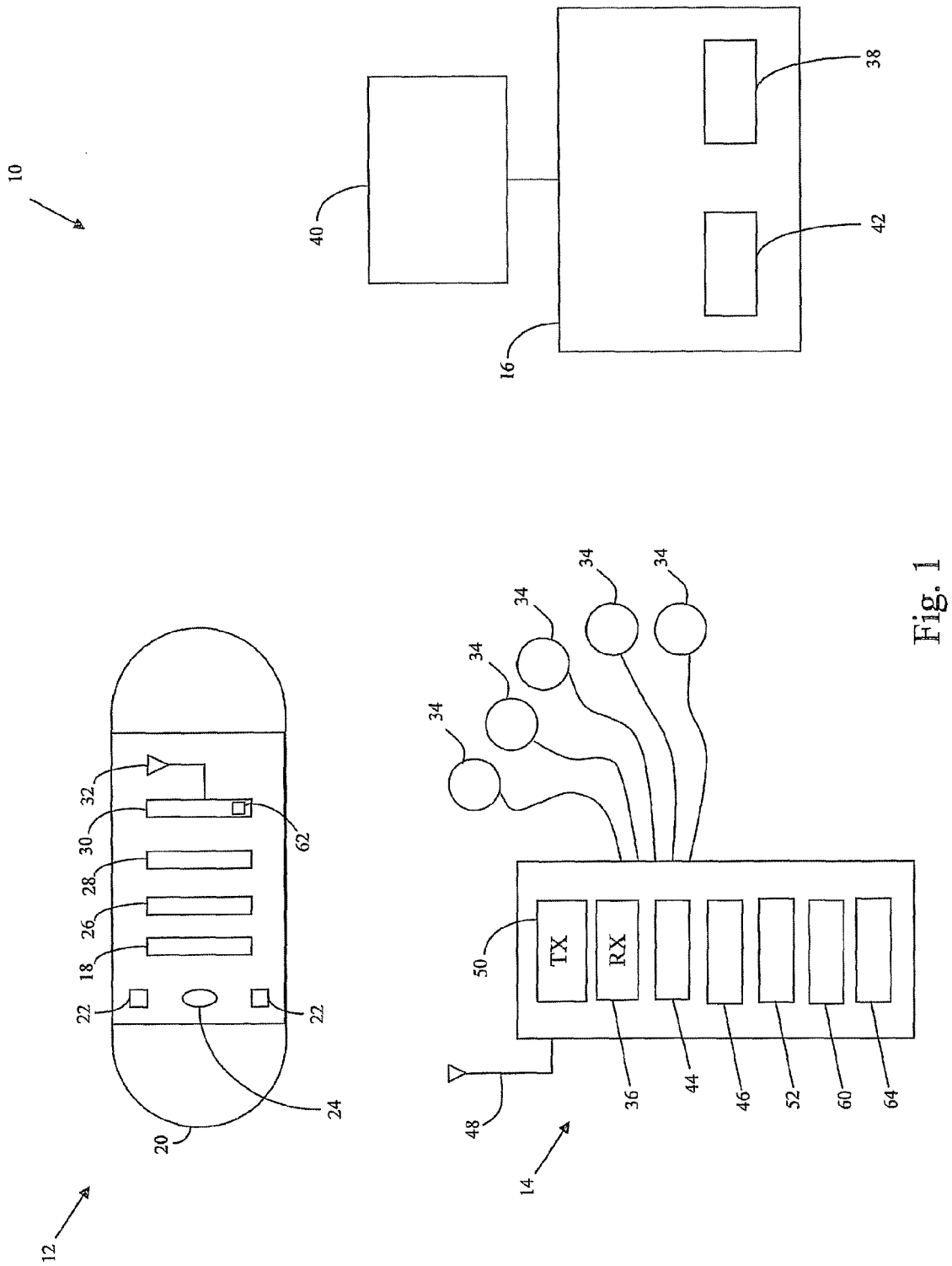
FIG. 1 is a simplified conceptual illustration of an in-vivo sensing system according embodiments of the present invention.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

The device of the present invention may be used with an imaging system or device such as that described in U.S. Pat. No. 5,604,531 entitled "In Vivo Video Camera System," which is incorporated herein by reference. A further example of an imaging system and device with which the device of the present invention may be used is described in U.S. Pat. No. 7,009,634 entitled "Device for In Vivo Imaging," which is incorporated herein by reference. For example, a swallowable imaging capsule such as that described in U.S. Pat. No. 7,009, 634, may be used in the present invention.

Reference is made to FIG. 1, showing in-vivo imaging system 10 according to embodiments of the present invention. The in-vivo imaging system 10 includes an in-vivo imaging device 12, a data recorder 14 and a work station 16. In some embodiments, the in-vivo imaging device 12 may be a wireless device. In some embodiment, the in-vivo imaging device 12 may be autonomous. In some embodiments, the in-vivo imaging device 12 may be a swallowable capsule for imaging the gastrointestinal tract of a patient after the patient has swallowed the in-vivo imaging device 12. However, other body lumens or cavities may be imaged or examined with the in-vivo imaging device 12.

The in-vivo sensing device 12 may include at least one sensor such as an imager 18 for capturing image data in the form of image frames of images of the gastrointestinal tract or other body lumens or cavities, a viewing window 20, one or more illumination sources 22, an optical system 24, a power supply such as a battery 26, a processor 28, a communication unit 30, and an antenna 32 connected to the communication unit 30. In some embodiments, the communication unit 30 may be a transmitter. In other embodiments, the communication unit 30 may be a transceiver (i.e., transmitter and receiver). The imager 18 may be, or may contain, a CMOS imager. Alternatively, other imagers may be used, e.g. a CCD imager or other imagers. The illumination sources 22 may be Light Emitting Diodes (LED) or other suitable illumination sources for illuminating a target area from which images are to be captured. The target area may be an area of the gastrointestinal tract or other body lumens or cavities of the patient.

As the in-vivo sensing device 12 traverses the gastrointestinal tract or other body lumens, the imager 18 may capture a series of images at a rate of a given number of frames per second to form a data stream, forming the frames of a video movie. Each image frame may be associated with image data representative of an image of a target area being imaged. The image data and or other data captured by the in-vivo sensing device 12 may be transmitted as a data signal in data frames by wireless connection, e.g. by a wireless communication channel, by the communication unit 30 via the antenna 32, from the in-vivo sensing device 12 and received by the data recorder 14 via one or more receiving antennas 34, for example an antenna array that may, for example, at least partially surround the patient. The receiving antennas 34 are connected to a data recorder receiver 36. The received data signal may be, for example, downloaded to the workstation 16 for processing by a work station processor 38, and for analysis, and display, for example, on a display unit 40. The received processed data may be stored on a workstation storage unit 42. Downloading and/or processing in the workstation 16 may occur off-line for example after the data recorder 14 has completed receiving and recording the data signal received from the in-vivo sensing device 12, or may occur in real-time.

In some embodiments, the data recorder 14 may include display capability, for example the data recorder 14 may include a viewer 44 for viewing information and/or images, for example information and/or images transmitted by the in-vivo imaging device 12. In another embodiment, processing and/or analysis may be performed at least partially within the data recorder 14 by a data recorder processor 46. In some embodiments, the data recorder 14 may include a data recorder transmitting antenna 48 connected to a data recorder transmitter 50 for transmitting instructions to the in-vivo sensing device 12. In some embodiments, the data recorder 14 may include a warning unit 52 which may be a visible warning unit, including an illumination source, or an audio warning unit including a loudspeaker.

Figure 2:
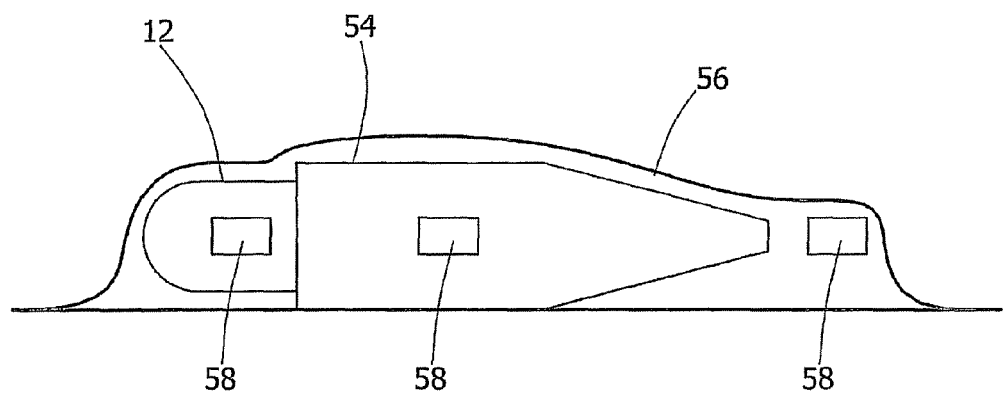
FIG. 2 is an illustrative side view of an in-vivo imaging device in a blister pack in accordance with embodiments of the present invention.

Reference is now made to FIG. 2. In some embodiments, prior to deployment, the in-vivo sensing device 12 may be held in a holder 54 located in a container, such as a blister pack 56, in a non-operative state so that no power, or only a negligibly small amount of power, is withdrawn from the battery 26. According to one embodiment when the in-vivo imaging device 10 is removed from the holder 54, prior to deployment, it may become operative. According to another embodiment, the in-vivo sensing device 12 may be activated, i.e. may be made operative, by other means, prior deployment. The activated in-vivo sensing device 12 may capture and transmit image data and/or other data and the transmitted captured data may be received by the data recorder, as described above.

In accordance with some embodiments, the in-vivo sensing device 12 and/or the holder 54 and/or the blister pack 56 may be provided an identifier element 58 which has an identifier code, such as, for example, but not limited to, a numeric string of characters or an alphanumeric string of characters. In accordance with one embodiment, the identifier element 58 may be a bar code, in accordance with another embodiment the identifier unit may be an RFID (radio frequency identification) chip. In accordance with some embodiments, prior to a patient swallowing the in-vivo sensing device 12 the identifier code may be obtained and inputted to the data recorder 14 where it may be stored in a data recorder memory 60. In some embodiments, the obtained identifier code may be first inputted to the work station 16 and stored in the workstation storage unit 42 and then inputted to the data recorder 14 by connecting the data recorder to the work station, or by wirelessly transmitting the identifier code from the work station 16 to the data recorder. In embodiments where the identifier element 58 is a bar code, the identifier code may be obtained using a barcode reader. In embodiments where the identifier element 58 is an RFID chip, the identifier code may be obtained using an RFID reader. In some embodiments, the in-vivo sensing device 12 may include a device memory 62. The device memory 62 may be a non-volatile memory such as, for example, a read-only memory or a flash memory. The device memory 62 may be incorporated in the processor 28.

According to another embodiment, the in-vivo sensing device 12 may not require the identifier element 58. For example, typically the in-vivo sensing device 12 may start transmitting images as soon as it is removed from its packaging. An external device, such as the data recorder 14 or the work station 16 may include a display which presents the images captured by the in-vivo sensing device 12, preferably in real-time. The images may be viewed by a user or a health care specialist, and may be associated o the specific in-vivo sensing device 12 according to the images viewed in the display. For example, the user may verify that the data recorder 14 is indeed recording images from the correct sensing device by pointing the sensing device at himself and see his image on the display, or pointing it at another distinct object. In another embodiment, the user may point the sensing device at a predetermined image, and based on image processing, the data recorder 14 may associate the specific sensing device to the received images. Further, the user may click a button, provided for example on data recorder 14 to lock the association of the specific sensing device to the data recorder. Such detection may be quite simple to perform, since the user may receive real time feedback from the correct sensing device.

Figure 3:
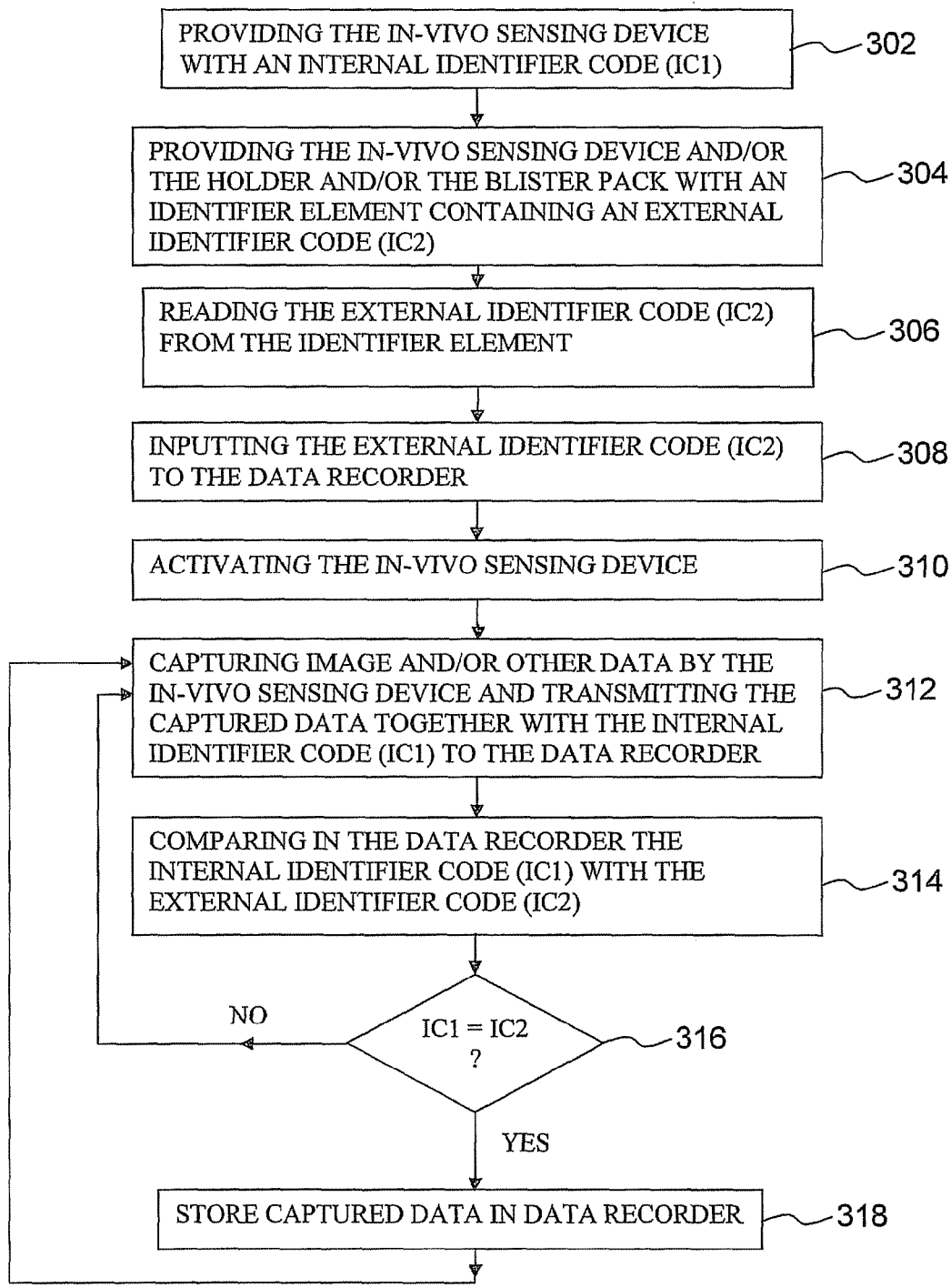
FIG. 3 is a simplified block diagram illustration of a method according to embodiments of the invention of identifying an in-vivo sensing device by correlating received data with the in-vivo sensing device.

FIG. 3 is a simplified block diagram illustration of a method according to embodiments of the invention of identifying an in-vivo sensing device by correlating received data with the in-vivo sensing device. The method includes the steps of: (i) Providing the in-vivo sensing device 12 with an internal identifier code IC1 and storing the internal identifier code IC1 in the device memory 62 (step 302) (ii) providing the in-vivo sensing device 12 and/or the holder 54 and/or the blister pack 56 with an identifier element 58, the identifier element 58 containing an external identifier code IC2 (step 304); (iii) prior to deployment, for example swallowing of the in-vivo sensing device 12 by a patient, reading the external identifier code IC2 from the identifier element 58 (step 306); (iv) inputting the external identifier code IC2 to the data recorder 14 and saving the external identifier code IC2 in the data recorder memory 60 (step 308); The external identifier code IC2 may be input to the data recorder 14 by a human-machine interface accepting input from a user (for example using a keyboard or input buttons), or by using an input device of a workstation which may be connected to the data recorder. (v) activating and deploying the in-vivo sensing device 12 (step 310). In accordance with some embodiments the in-vivo sensing device 12 may be activated by removing it from the blister pack 56. In some embodiments, the in-vivo sensing device 12 may include a magnetic switch which is controlled by an external magnet. The external magnet may be located, for example, in the blister pack 56 in the vicinity of the magnetic switch. On removing the in-vivo sensing device 12 from the blister pack 56 the external magnet is distanced from the magnetic switch which changes its state thereby electrically activating the in-vivo sensing device 12. The method also includes the steps of (vi) capturing image data and or other data by the in-vivo sensing device 12 and transmitting, together with the internal identifier code IC1, the captured data to the data recorder 14 (step 312); (vii) comparing the internal identifier code IC1 received by the data recorder 14 from the in-vivo sensing device 12 with the external identifier code IC2 read from the identifier element 58 (step 314). Next, a decision is made (step 316). If the internal identifier code IC1 matches the external identifier code IC2 then the received captured data (image data and or other data) may be stored in the data recorder memory 60 (step 318) and control may be returned to step 312 so that further data may be captured by the in-vivo sensing device 12 and transmitted to the data receiver 14. On the other hand, if the internal identifier code IC1 does not match the external identifier code IC2, then the data received by the data recorder 14 has been received from a different in-vivo sensing device and the received data is not stored in the data recorder memory 60 and control may be returned to step 312 so that further data may be captured by the in-vivo sensing device 12 and transmitted to the data receiver 14 (step 312). In this way, only image data and or other data received from a designated in-vivo sensing device 12 may be stored by the data recorder 14. The designated in-vivo sensing device 12 being the in-vivo sensing device 12 whose internal identifier code IC1 matches the external identifier code IC2. In those embodiments in which the in-vivo imaging device 12 is a swallowable capsule for imaging the gastrointestinal tract of a patient, the designated in-vivo imaging device 12 is the in-vivo sensing device swallowed by a given patient.

Figure 4:
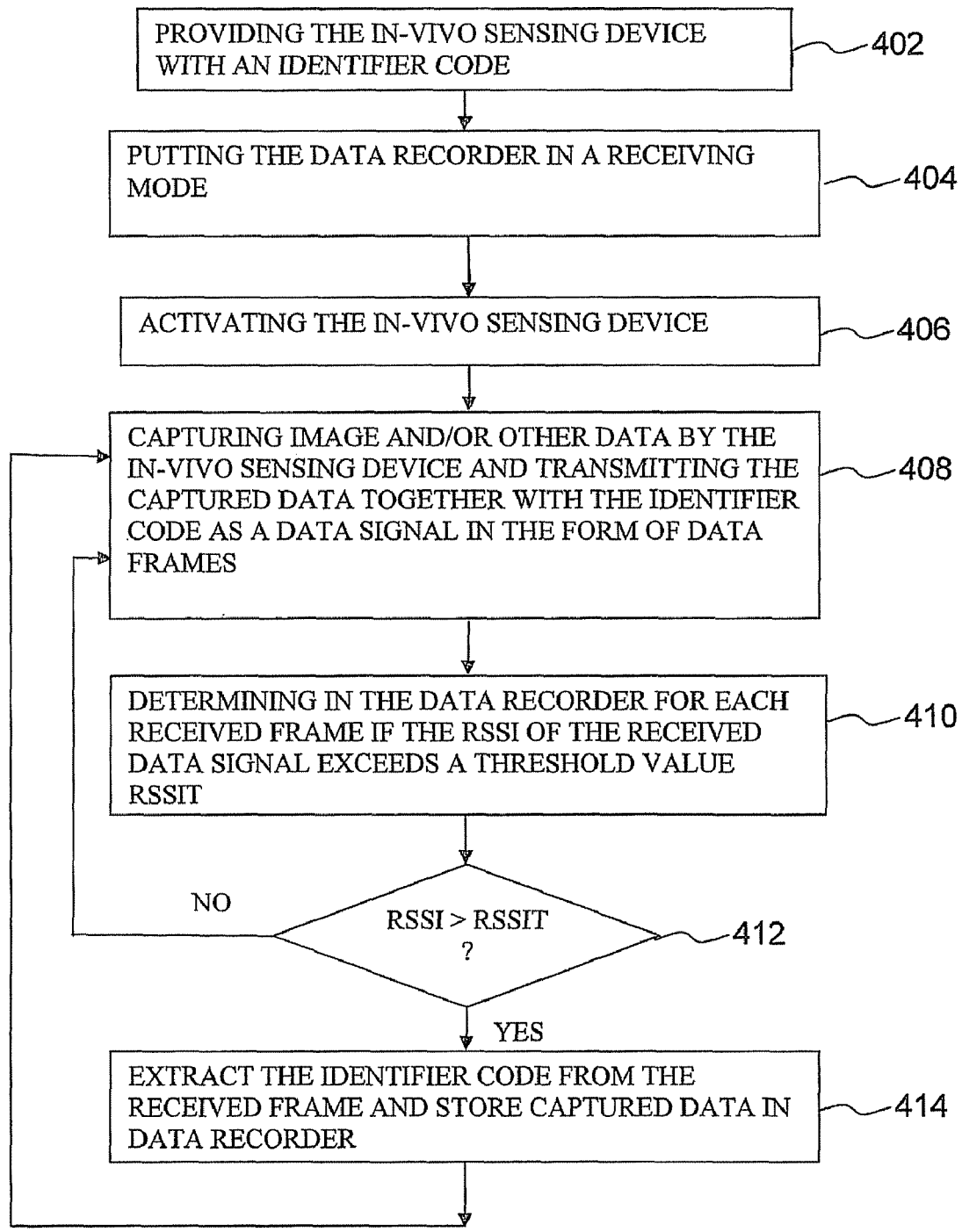
FIG. 4 is a simplified block diagram illustration of a method according to some embodiments of the invention for identifying an in-vivo sensing device based on RSSI.

In accordance with some embodiments, the data recorder 14 may be provided with a Received Signal Strength Indication (RSSI) unit 64 and may determine if the received data signal (in the form of data frames containing the internal identifier code of the in-vivo sensing device, the captured image data and or other data) is received from the designated in-vivo sensing device 12 based on a Received Signal Strength Indication. FIG. 4 is a simplified block diagram illustration of a method according to some embodiments of the invention for identifying an in-vivo sensing device based on RSSI. The method includes the steps of: (i) providing the in-vivo sensing device 12 with an identifier code and storing the identifier code in the device memory 62 (step 402); (ii) putting the data recorder 14 in a receiving mode (step 404); (iii) activating the in-vivo sensing device 12 (step 406); capturing image and/or other data by the in-vivo sensing device 12 and transmitting the captured data together with the identifier code as a data signal in the form of data frames (step 408); determining in the data recorder for each received frame if the RSSI of the received data signal exceeds a threshold value RSSIT (step 410). Next, a decision is made (step 412). If the RSSI of the received data signal exceeds the threshold value RSSIT for a received frame then the identifier code of the in-vivo sensing device 12 is extracted from the received frame and saved in the data recorder memory 60 along with the received captured data (step 414) and control is returned to step 408 so that further data may be captured by the in-vivo sensing device 12 and transmitted to the data receiver 14 (step 408). On the other hand, if the RSSI of the received data signal does not exceed the threshold value RSSIT, then the data received by the data recorder 14 has been received from a different in-vivo sensing device and control is returned to step 408 so that further data may be captured by the in-vivo sensing device 12 and transmitted to the data receiver 14 (step 312). These steps (408-412) may be performed during the entire in-vivo sensing procedure, or only during a preset time period, for example for the first 5 or 10 minutes of an in vivo sensing procedure. If the RSSI is checked for each frame throughout the entire in-vivo sensing procedure, an offline process may analyze the identifier code which is received in the data frames, for example in step 414, to determine whether to store the data frames received with the specific identifier code or to discard them. The offline analysis of the identifier code may be performed either in the data recorder or in a workstation operably connected to it. The RSSI may be checked only during an initial predetermined time interval, then only frames with RSSI>RSSIT may be stored in the data recorder. After the predetermined time interval is expired, the identifier contained in the stored frames (those frames which had RSSI larger than RSSIT) is analyzed, and the designated device is selected based on the largest number of frames containing the same identifier code. For example, a histogram of the number of frames may be created, wherein each column in the histogram represents a different detected identifier code. The method may include selecting the internal identifier code which is contained in the largest number of frames; and determining the designated in vivo device based on said internal identifier code. In this case, for frames received after the predetermined time interval, analysis of the identifier code may preferably be done online, during the recording of the data frames made in an in vivo sensing procedure. In this way, only image data and/or other data received from the designated in-vivo sensing device 12 may be stored by the data recorder 14. The designated in-vivo sensing device 12 being the in-vivo sensing device 12 for which the RSSI of the received data signal exceeds the threshold value RSSIT. In other words, the designated in-vivo sensing device 12 is identified by its proximity to the receiving antennas 34. The concept of using the highest RSSI is based on the assumption that the designated capsule is located closer to the DR than other capsules, therefore its RSSI may be relatively high when compared with other detected data signals which may be sent by other sensing devices. Therefore, in a preferable embodiment, step 408 may be preceded by the further step of bringing the in-vivo sensing device 12 close to the receiving antennas 34.

According to one embodiment, a different method may be used to associate the in vivo sensing device to a specific data recorder. The method may include the steps of: (i) providing the in-vivo sensing device 12 with an identifier code and storing the identifier code in the device memory 62; (ii) putting the data recorder 14 in a receiving mode; (iii) activating the in-vivo sensing device 12; capturing image and/or other data by the in-vivo sensing device 12 and transmitting the captured data together with the identifier code as a data signal in the form of data frames. After a preset time period, for example after the first 5 minutes of powering up the data recorder or the in-vivo sensing device, a histogram of the received number of data frames (which include an identifier code) may be calculated. For example, only frames sent by a sensing device which was powered up less than the preset time period may be taken into account in the histogram calculation. After the designated time period has expired, a decision may be made, for example associating an in vivo sensing device to the data recorder based on the largest number of frames received in the data recorder from a specific sensing device. The device is then set as the designated capsule. In one embodiment, only frames received with the same device identifier code may be accepted by the data recorder.

In some embodiments, the method of identifying the designated in-vivo sensing device 12 may include transmitting the "number of frames captured" (determined by a frame counter in the in-vivo sensing device 12) in the data signal. Since the designated in-vivo sensing device 12 is generally activated only shortly before deployment then the "number of data frames captured" should be a relatively small number (e.g., less than 30). If a data signal is received by the data recorder 14 for which the "number of data frames" is very large (e.g., greater than 100 or greater than 15,000), then it could be an indication that the data signal was not received from the designated in-vivo sensing device 12. A threshold value of the number of data frames may be configured according to, for example, the type of the procedure that the patient is about to undergo, or according to a type of sensing device (and/or frame rate) that is used. This concept may be used as another embodiment, for example: after power-up of the data recorder, it checks all incoming frames. This may be performed during a preset interval, for example the first 10 minutes of operation. During this interval, data frames including a frame counter with a value less than a preset threshold value may be accepted. Received frames with a frame counter value which is greater than the preset threshold may be discarded. When the time interval is expired, a decision may be made, for example in the data recorder, after checking all the accepted data frames and their corresponding device identifier. The identifier of the device which has the largest number of data frames received (and accepted) may be selected as the designated sensing device for the current in vivo sensing procedure, and may be associated to the data recorder. After the association of the sensing device to the data recorder in the current in vivo sensing procedure, only data frames arriving from the selected in vivo sensing device (e.g., having the same identifier code as the selected sensing device) may be accepted and recorded by the data recorder.

In some embodiments, it may be also possible to combine the frame counter with the RSSI. For example, during a preset time period after the power-tip of the data recorder, only frames which have an RSSI value that is larger than RSSIT and frame counter which is less than the frame counter threshold may be counted. After the preset interval is over, a decision is made based on the largest number of counted frames arriving from the same sensing device (e.g., with the same identifier code in the frames).

Figure 5:
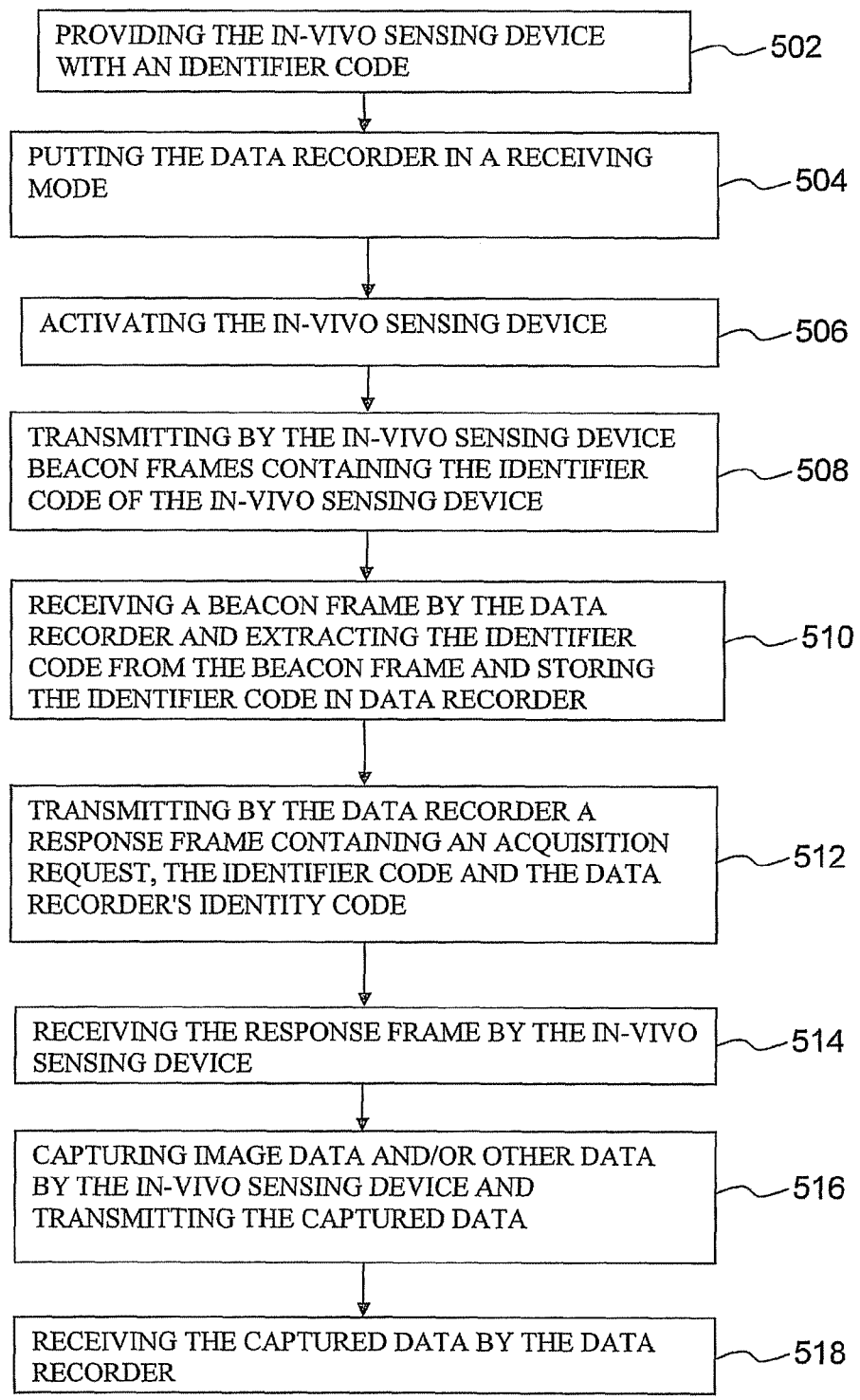
FIG. 5 is a simplified block diagram illustration of another method according to embodiments of the invention of identifying an in-vivo sensing device.

FIG. 5 is a simplified block diagram illustration of another method according to embodiments of the invention of identifying an in-vivo sensing device. The method includes the steps of: (i) providing the in-vivo sensing device 12 with an identifier code and storing the identifier code in the device memory 62 (step 502); (ii) putting the data recorder 14 in a receiving mode (step 504); (iii) activating the in-vivo sensing device 12 (step 506); (iv) transmitting by the in-vivo sensing device 12 beacon frames that contain the identifier code (step 508). At this stage the in-vivo sensing device 12 may not be operating in a normal acquisition mode and may not be capturing data. There are several advantages to transmission of beacon frames instead of sensed data. Beacon frames which do not include image data, are usually small, and are transmitted in a shorter time than in vivo sensed data frames. Therefore the beacon transmission may interfere less with other sensing devices' transmissions. In addition, transmission of beacon frames saves sensing device power compared to image or other sensed data transmission. Consequently, whilst the in-vivo sensing device 12 is in a beacon transmitting mode it may provide an indication that it is not ready for deployment. The indication may be by visible means, for example, by blinking very fast or very slow or by not blinking at all. The blinking may be performed by the illumination sources 22. Preferably, the patient undergoing the sensing procedure should wait until an indication is provided by the in-vivo sensing device 12 that it is ready for deployment. This may confirm that the in-vivo sensing device 12 has been acknowledged by the data recorder and associated to it for the current procedure. The method includes the further steps of: (v) receiving a beacon frame by the data recorder 14, extracting the identifier code from the beacon frame and storing the identifier code in the data recorder 14 (step 510); (vi) transmitting by the data recorder 14 a response frame containing an acquisition request, the identifier code and the data recorder's identity code (step 512); receiving the response frame by the in-vivo sensing device 12 (step 514); (vii) capturing image data and/or other data by the in-vivo sensing device 12 and transmitting the captured data (step 516); and receiving the captured data by the data recorder (step 518). In step 514, as a consequence of the in-vivo sensing device 12 receiving the acquisition request (contained in the response frame), the in-vivo sensing device 12 changes modes of operation from a beacon transmitting mode to a data capturing mode. In step 516, the transmitted captured data may be transmitted by the in-vivo sensing device 12 together with the in-vivo sensing device identifier code. In some embodiments, the transmitted captured data may be transmitted together with the in-vivo sensing device identifier code and the data recorder identifier code. If step 516 includes transmitting the identifier code and/or the identity code, then step 518 may include receiving these codes. When the data recorder 14 receives captured data in step 518, then it has effectively acquired the designated in-vivo sensing device 12 and the data recorder provides an external indication that this is the case. Such an external indication may be the blinking of data recorder illumination sources. Alternatively, part of the data recorder viewer 44 may blink and/or may present a suitable notification. In some embodiments, the identifier code of the acquired in-vivo sensing device 12 may be displayed on the data recorder viewer 44.

Methods described in this patent may be performed on-line, for example during the capturing of sensed data by the in vivo sensing device. Determination of the designated capsule may either made immediately, as described in the beacon method illustrated in FIG. 5, or after a predefined time interval during which data may be collected and then analyzed. However, these methods can also be activated off-line, wherein all received data may be recorded in the data recorder, and the analysis of the recorded data is performed by a processor, such as a processor in a workstation, after the in vivo sensing procedure has ended. The determination of the designated in vivo sensing device may be based on different criteria, as described hereinabove, such as:

The largest number of data frames in an initial time interval, which have the same sensing device identifier;

The largest number of data frames which are above a threshold RSSI value in a predetermined time interval, the frames having the same sensing device identifier;

The largest number of data frames having the same sensing device identifier in the entire data recording; or The largest number of data frames having the same sensing device identifier, and also having a frame counter or 'number of transmitted frames' that may be below a specific threshold.

Data frames that are do not have the identifier code as the designated device may be discarded, for example by the external processor.

While the present invention has been described with reference to one or more specific embodiments, the description is intended to be illustrative as a whole and is not to be construed as limiting the invention to the embodiments shown. It is appreciated that various modifications may occur to those skilled in the art that, while not specifically shown herein, are nevertheless within the scope of the invention.

What is claimed is:

1. A method for associating data obtained by a data recorder to a designated in-vivo sensing device comprising:
   providing the designated in-vivo sensing device with an internal identifier code for the designated in-vivo sensing device;
   receiving a data signal in a form of a plurality of data frames from an in-vivo sensing device, each of said frames comprising an internal identifier code for the in-vivo sensing device;
   determining for each of said frames if a Received Signal Strength Indication (RSSI) of the corresponding received data signal exceeds a threshold value;
   for each of said frames, extracting said internal identifier code for the in-vivo sensing device from said frame if the RSSI exceeds the threshold value;
   selecting an internal identifier code which is contained in a largest number of frames from the frames having RSSI exceeding the threshold value, being the selected internal identifier code;
   identifying the designated in-vivo sensing device based on the selected internal identifier code;
   determining whether the received data signal is received from the designated in-vivo sensing device based on said selected internal identifier code; and
   if the data signal is received from the designated in-vivo sensing device, storing the data signal in a data recorder.

2. The method of claim 1 wherein the data frames are beacon frames.

3. The method of claim 1 wherein the data signal further comprises image data.

4. The method of claim 1 wherein determining if the received data signal is received from the designated in-vivo sensing device is performed online during an in vivo sensing procedure.

5. The method of claim 1 wherein the steps of determining for each of said frames if the RSSI exceeds a threshold value and extracting said internal identifier code are performed during an initial predetermined time interval.

6. An in-vivo sensing system for associating data obtained by a data recorder to a designated in-vivo sensing device, the system comprising:
   an external data recorder provided with a Received Signal Strength Indication (RSSI) unit, the external data recorder to:
     receive a data signal in a form of a plurality of data frames from at least one in-vivo sensing device, each of said frames comprising an internal identifier code for the in-vivo sensing device;
     determine, for each of said frames, if a Received Signal Strength Indication (RSSI) of the corresponding received data signal exceeds a threshold value;
     for each of said frames, extract said internal identifier code for the in-vivo sensing device from said frame if said RSSI exceeds said threshold value;
     select an internal identifier code which is contained in a largest number of frames from the frames having RSSI exceeding the threshold value, being the selected internal identifier code;
     determine said designated in-vivo sensing device based on said selected internal identifier code;
     determine whether the received data signal is received from the designated in-Vivo sensing device based on said selected internal identifier code; and
     store data received from said designated in-vivo sensing device,
   wherein the designated in-vivo sensing device comprises an imager for capturing image data, an illumination source, a communication unit comprising an antenna for wirelessly transmitting data and memory for storing an internal identifier code for the designated in-vivo sensing device.

7. The in-vivo sensing system of claim 6, wherein the external data recorder determines for each of said frames if the RSSI exceeds a threshold value and extracts said internal identifier code for the in-vivo sensing device during an initial predetermined time interval.

8. The in-vivo sensing system of claim 6, wherein the data frames are beacon frames.

9. The in-vivo sensing system of claim 6, wherein the data signal comprises image data.

10. The in-vivo sensing system of claim 6, wherein the external data recorder is to determine, online during an in vivo sensing procedure, if the received data signal is received from the designated in-vivo sensing device.

* * * * *